United States Patent [19]

Handt et al.

[11] 4,413,988
[45] Nov. 8, 1983

[54] SHORT-TUBING SET GRAVITY POWERED PERITONEAL CYCLER

[76] Inventors: Alan E. Handt, 705 Pineview, Zionsville, Ind. 46077; Stephen R. Ash, 2500 N. 400 East, Lafayette, Ind. 47905

[21] Appl. No.: 372,457

[22] Filed: Apr. 28, 1982

[51] Int. Cl.³ .............................................. A61M 5/00
[52] U.S. Cl. ..................................... 604/29; 604/27; 604/31; 604/131
[58] Field of Search ................................... 604/27–34, 604/36, 131, 141; 128/DIG. 12

[56] References Cited

U.S. PATENT DOCUMENTS

| | | | |
|---|---|---|---|
| 2,761,445 | 9/1956 | Cherkin | 128/DIG. 12 X |
| 3,151,616 | 10/1964 | Selfon | 604/131 |
| 3,647,117 | 3/1972 | Hargest | 604/131 X |
| 3,670,926 | 6/1972 | Hill | 604/131 X |
| 3,709,222 | 1/1973 | DeVries | 604/29 X |
| 3,783,866 | 1/1974 | Tirkkonen | 604/29 |
| 3,872,863 | 3/1975 | Lasker et al. | 604/29 |
| 3,895,741 | 7/1975 | Nugent | 604/141 X |
| 3,938,514 | 2/1976 | Boucher | 604/28 |
| 4,096,859 | 6/1978 | Agarwal et al. | 604/28 |
| 4,240,408 | 12/1980 | Schael | 604/28 |
| 4,306,976 | 12/1981 | Bazzato | 604/28 X |
| 4,326,526 | 4/1982 | Buck et al. | 604/29 |
| 4,337,769 | 7/1982 | Olson | 604/131 |

FOREIGN PATENT DOCUMENTS

WO80/02706 12/1980 PCT Int'l Appl. ............... 604/29

Primary Examiner—C. Fred Rosenbaum
Assistant Examiner—Michelle N. Lester
Attorney, Agent, or Firm—Woodard, Weikart, Emhardt & Naughton

[57] ABSTRACT

A machine for infusion and withdrawal of fluid from the peritoneal cavity of a person. A plurality of bags of fluid each rests atop spaced apart trays arranged in a stack and supported by a vertical secondary frame slidably mounted in a main frame. Moveable pins mounted to the main frame sequentially support the secondary frame and an adjacent tray until the entire secondary frame and stack of trays move downwardly pass the pins. The trays include clamping mechanisms engaged with the tubular ports of each bag to control fluid flow through the port of a particular bag supported by a tray. Pins are fixedly mounted to bars slideably mounted to the main frame and moved either manually or by means of a solenoid to control movement of the trays and secondary frame and thus fluid flow.

16 Claims, 12 Drawing Figures

SHORT-TUBING SET GRAVITY POWERED PERITONEAL CYCLER

BACKGROUND OF THE INVENTION

This invention is in the field of medical machines for sequentially emptying and refilling bags of fluid for peritoneal dialysis. Recently, there has been a resurgence of interest in the nephrology community in peritoneal dialysis. This method of treatment of kidney treatment is somewhat slower than hemodialysis since it utilizes the diffusive properties of the peritoneal membrane (the shiny, thin membrane which covers all of the abdominal cavity contents) for transfer of body waste. The peritoneum is utilized as an effective excretory organ by placing a sterile balanced-salt solution into the abdominal cavity and leaving the solution therein for a certain period or dwell time. During the dwell time, waste molecules from the blood diffuse across the peritoneal membrane into the clear salt solution.

The relatively slow nature of peritoneal dialysis as compared to hemodialysis or the extracorporeal purification of blood may be offset by schedules of dialysis allowing for continuous treatment of the patient. In 1975, Popovich and Moncrief described an exchange method for peritoneal dialysis in which two liters of fluid are placed in the patient's abdomen and left for a period of four to eight hours. Subsequently, the fluid was drained and two liters of new fluid was placed into the abdomen. A modification of this procedure by Oreopoulos, in 1977, included use of peritoneal solution in two liter bags. The bags could then be rolled up and carried by the patient in the empty state during the dwell time. These patients were ambulatory and required only one bag connection for both infusion and drainage of fluid. This method of dialysis has expanded widely, with over 5,000 patients in the United States now receiving such dialysis. The method is from a chemical standpoint the most effective method of treatment of renal failure by dialysis. It is known as "Continuous Ambulatory Peritoneal Dialysis", (CAPD) used in ambulatory outpatients. In a hospital setting, for patients who are in an intensive care unit or ward situation, the method is known as "Continuous Equilibrium Peritoneal Dialysis", (CEPD).

The significant limitation of this novel procedure has been the development of peritonitis by the patients, in which peritonitis is mostly induced by chance contamination of the spike during insertion and removal from the tubular outlet of the bag of fluid. To avoid the infection, meticulous care must be taken by the patient or hospital staff during the spike exchange period. The usual spike exchange and drainage procedure takes approximately ½ hour resulting in 2 to 3 hours of manpower input per day. Such a procedure in a hospital setting is not only very costly but in many cases ineffective in avoiding infection.

An alternate mechanized method of such peritoneal fluid cycling has been proposed by Diaz-Buxo wherein a machine performs the cycling of peritoneal fluid during the nighttime hours and allows the patient to be ambulatory with a two liter residual peritoneal fluid in the abdomen during daytime hours. Use of a machine compresses the time necessary for performance of continuous peritoneal dialysis to two segments, one setting of the machine and one in taking the machine down and sealing off the abdominal cavity tubing. Several types of machines have been developed. The R-O machine is a mechanical proportioning machine producing sterile water and mixing it in a 1–20 dilution with concentrate. The American Medical Products Machine is a gravity powered machine utilizing 4 to 8 bags or bottles of fluid suspended above the bed of the patient. A large drainage bag of 4 to 12 liters attached to the same tubing set is required and is suspended below the bed of the patient.

All of the machines to accomplish the peritoneal dialysis have certain disadvantages. Some of the machines are somewhat complicated requiring resterilization after each use and utilizing electrical or mechanical scales for determining outflow volumes. A significant number of "alarms" may be expected during each operation. Some machines require a rather large and long tubing set which must be connected to the bottle suspended at a meter above the bed and with a drainage bag below the bed. In addition, a "warming bag" is utilized for warming fluid before the fluid enters the abdomen of the patient. The outflow volume must be electro-mechanically determined by a sensitive weighing mechanism which must weigh up to the total of 12 liters outflow volume. Some of the machines are rather bulky weighing over 40 lbs without fluid and standing over six feet tall when assembled. In certain cases, the bag connections must be made with the same type of manual clamps utilized for CAPD in the home since there is no firm fixation of the "nipple" or spike inlet of the bag when placed on the machine. Instead, the bags are merely hung vertically at the top of the machine and the critical entrance to the bag is a freely movable somewhat floppy position.

It would be ideal to have a cycler machine which utilizes a short tubing set just large enough to span the physical distance needed to separate the bags. For example, each bag need be separated only by about 4 inches when full. In order to achieve a short tubing section, it is necessary to have a physical method of compression of each bag or expansion of each bag and to rely on this force to fill and empty the bag rather than to utilize the position of each bag alone (above and below the abdomen) for generation of hydrostatic pressure. Such compression and drainage of each bag would necessarily require considerable amount of force if done by a piston or air pressure cycler. On the other hand, a considerable amount of force is present in the weight of the bag alone with six 2-liter bags weighing approximately 12 kilograms. By utilizing the weight of the entire fluid for compression of each bag, then the energy input to each bag would be six times that obtained from the weight of one bag's fluid alone. Heretofore, the potential energy of each 2-liter volume of fluid of a standard cycler is wasted once the fluid has drained into the drainage bag. The weight of fluid in such a gravity powered cycler could be utilized to augment infusion of further bags of fluid. By supporting the bag at a certain distance approximately 2 feet from the floor of the room, further energy may be gained from the bags as they inch their way towards the floor. Such a two foot elevation of the dialysis fluid still allows adequate drainage of the abdomen since there is significant intraperitoneal pressure of 10 to 20 cm of water, with the patient elevated approximately two to three feet off the floor by his bed or chair. Disclosed herein is such a machine which utilizes a short tubing set, avoids the necessity of heating of the drainage bag and returns the fluid to the same bag from which it is delivered. The cycler is gravity powered, utilizing energy obtained from the weight of bags which have already been drained, as well as those which are yet to be used in the abdomen. The cycler is therefore a Short-Tubing Set Gravity Powered Peritoneal Cycler or STS-GPC.

SUMMARY OF THE INVENTION

One embodiment of the present invention is a cycling machine for infusion and withdrawal of fluid from a person comprising a main frame, a secondary frame slidably mounted to the main frame and including a plurality of shelves; a vertical stack of trays each resting atop an associated shelf of the plurality of shelves with the trays being spaced apart to each receive a separate associated bag of fluid, stop means movably mounted on the main frame initially positioned beneath the stack and releaseably engagable with the secondary frame and also releaseably engageable with the most adjacent tray of the stack to hold the adjacent tray as the secondary frame and supported trays and bags fall downwardly pressing the associated bag against the adjacent tray squeezing fluid therefrom, operator means engaged with the stop means and cyclically operable until all of the bags are drained and refilled to first release the stop means from the secondary frame which falls while the stop means holds the adjacent tray and to next move the stop means apart from the adjacent tray to catch and hold the secondary frame allowing the adjacent tray to fall back atop the associated shelf decompressing the associated bag to receive gravity inflow of fluid.

Another embodiment of the present invention is a short tube set gravity powered peritoneal cycler comprising a main frame, a plurality of bags of fresh fluid, a plurality of trays each sized to support one of the bags, a vertical frame slidably mounted in the main frame and having mounting planes each receiving one of the trays, a movable holder on the main frame to alternately hold a particular tray with bag as the vertical frame weighs downwardly thereon squeezing fresh fluid therefrom and then holding the vertical frame as the particular tray falls away from the vertical frame decompressing the bag on the particular tray which receives back waste fluid.

It is an object of the present invention to provide a short tubing set gravity powered peritoneal cycler.

Another object of the present invention is to provide a new and improved cycling machine for infusion and withdrawal of fluid from a person.

Another object of the present invention is to provide a relatively inexpensive compact peritoneal cycler.

Related objects and advantages of the present invention will be apparent from the following description of the preferred embodiment.

DESCRIPTION OF THE PREFERRED EMBODIMENT

Figure 1:
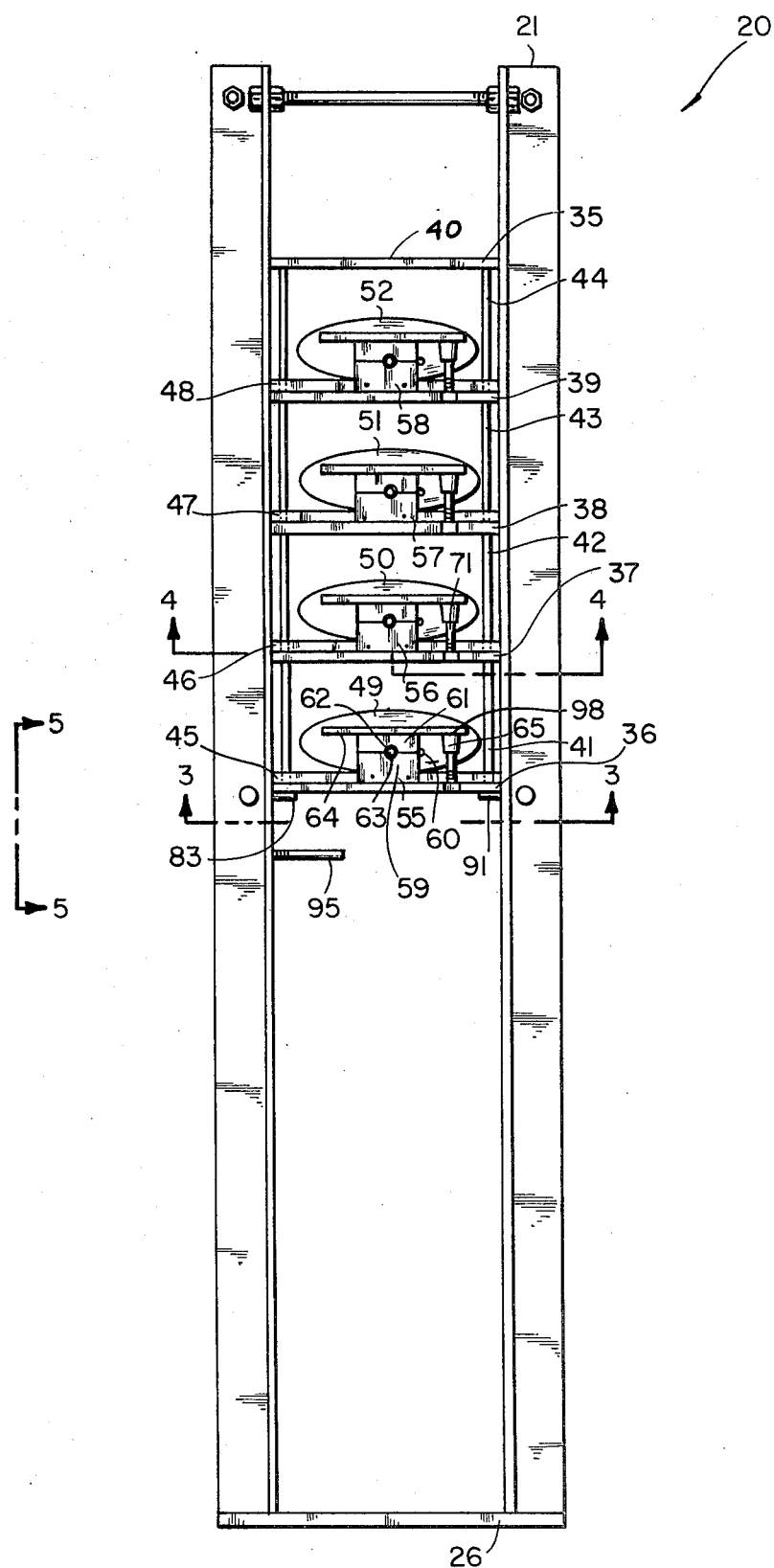
FIG. 1 is a front view of the short tubing set gravity powered cycler incorporating the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 2:
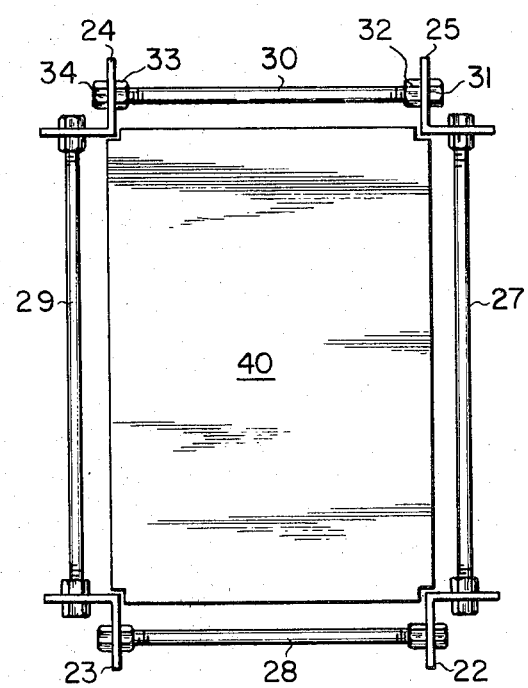
FIG. 2 is an enlarged top view of the device shown in FIG. 1.

Referring now more particularly to FIGS. 1 and 2, there is shown the short tubing set gravity powered peritoneal cycler 20 incorporating the present invention. Cycler 20 includes a main frame 21 having four right angle beams 22 through 25 fixably mounted a top base 26. Four cables or threaded rods 27 through 30 have opposite ends fixedly secured to each beam forming a generally rectangular channel extending from the top of the main frame downwardly to base 26. Conventional threaded fasteners are mounted to the opposite ends of the cables or threaded rods to secure the beams together. For example, hexagonally shaped nuts 31 and 32 are positioned on opposite sides of one wall of beam 25 threadedly receiving one end of threaded rod 30 preventing relative motion between the threaded rod and beam 25. Likewise, a second pair hexagonally shaped nuts 33 and 34 are threadedly received onto to the opposite end of rod 30 on opposite sides of the wall of beam 24.

A secondary frame 35 (FIG. 1) is slideably mounted to main frame 21 and includes a plurality of shelves 36 through 40 arranged in a vertical stack being spaced apart and fixedly secured together by means of a plurality of rods fixedly secured to the four corner portions of each shelf. For example, rod 41 has a bottom end fixedly attached to one corner portion of shelf 36 and a top end fixedly secured to corresponding corner portion of shelf 37. Likewise, rods 42, 43 and 44 are fixedly secured respectively to and between shelves 37 and 38, shelves 38 and 39 and shelves 39 and 40. The four vertical uprights or beams are spaced apart at the corners of a square about 8 inches by 13 inches. The uprights or beams are approximately 50 inches tall with the secondary frame 35 having a length of approximately 25 inches with a bottom square dimension of approximately 8 inches by 13 inches and having within it 5 or more parallel plates for supporting at 4 inch intervals a plurality of bags.

Figure 6:
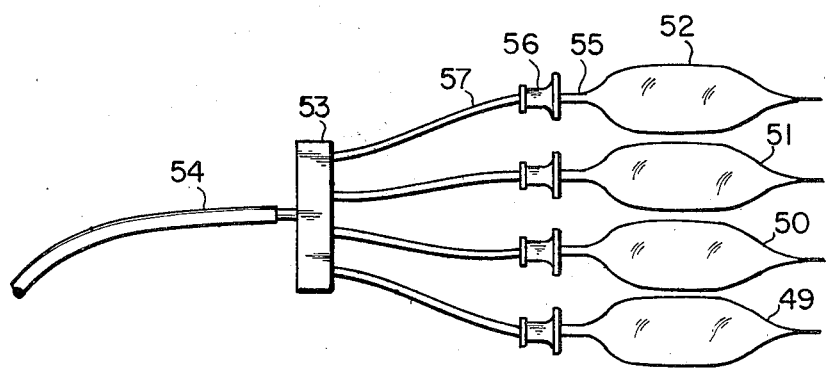
FIG. 6 is a diagram depicting the interconnections of the bags of fluid.

A vertical stack of trays 45, 46, 47 and 48 each rest atop respectively on associated shelf 36, 37, 38 and 39 with the trays being spaced apart to receive respectively a separate associated bag of fluid 49, 50, 51 and 52. Bags 49 through 52 are each connected by suitable tubing to a manifold 53 (FIG. 6) in turn connected to tubing 54 having its opposite end connected to the abdominal cavity of the patient. Each bag has a tubular outlet removably connectable to a spike in turn connected by a tube to manifold 53. For example, bag 52 includes a tubular outlet 55' connected by means of a conventional spike 56' to tubing 57' having its opposite end connected to manifold 53. Due to the short spacing of the trays 45 through 48 as well as the short downward travel of secondary frame 35, the tubing set depicted in FIG. 6 may be relatively short allowing for each bag to be first emptied and refilled before the next higher bag is emptied and refilled in sequential manner.

A clamping means is mounted to each tray and is engagable with the tubular port of each bag to control fluid flow therethrough. Clamps 55, 56, 57 and 58 are fixedly mounted to trays 45, 46, 47 and 48 and are engaged with the tubular ports of bags 49, 50, 51 and 52. Clamp 55 will now be described as being understood that a similar description applies to clamps 56 through 58. Clamp 55 has a bottom half portion 59 fixedly mounted by rivets or other suitale means to tray 45. A top half clamp portion 61 is hingedly mounted to bottom half portion 59 by hinge 60 and is pivotable from a closed position in the clockwise direction as viewed in FIG. 1 about hinge 60 to an open position. Two mating semi-circular recesses formed in clamp portions 59 and 61 form passage 62 through which tubular conduit 63 of bag 49 extends. Passage 62 is restricted clamping tubular conduit 63 shut and preventing fluid flow therethrough when the top half portion 61 of the clamp is pivoted downwardly atop the bottom half portion 59. Bar 64 is fixedly mounted atop the top half clamp portion 61 and has a right end portion 98, as viewed in FIG. 1, normally contacted by an upwardly projecting actuator 65 fixedly mounted atop shelf 36 and positioned to force bar 64 and the top half of clamp portion 61 to the closed position as shown in FIG. 1 whenever tray 45 rests atop shelf 36. End 98 is sufficiently weighed to cause bar 64 and the top half portion 61 to pivot clockwise around hinge 60 opening the clamp and allowing fluid flow through the tubular port of the bag whenever the tray upon which the bag is supported separates from or is spaced apart from the supporting shelf thereby relieving the pressure between bar 64 and actuator 65.

Figure 3:
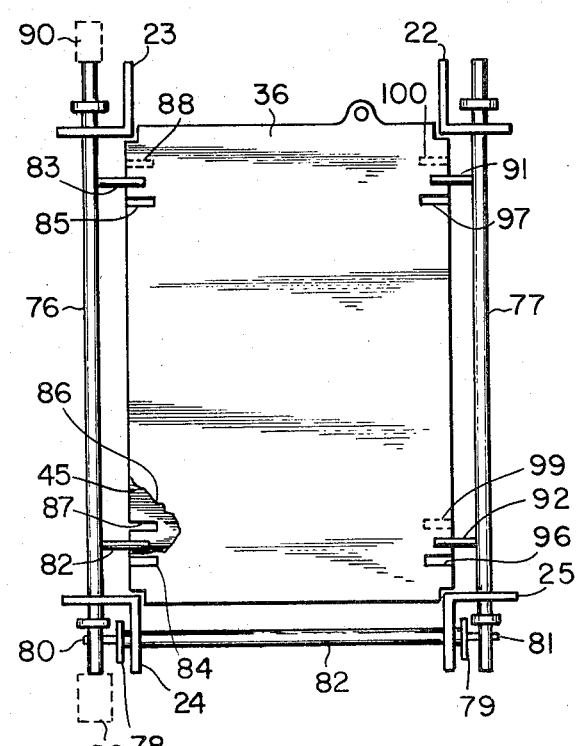
FIG. 3 is an enlarged fragmentary cross-sectional view taken along the line 3—3 of FIG. 1 and viewed in the direction of the arrows.
Figure 5:
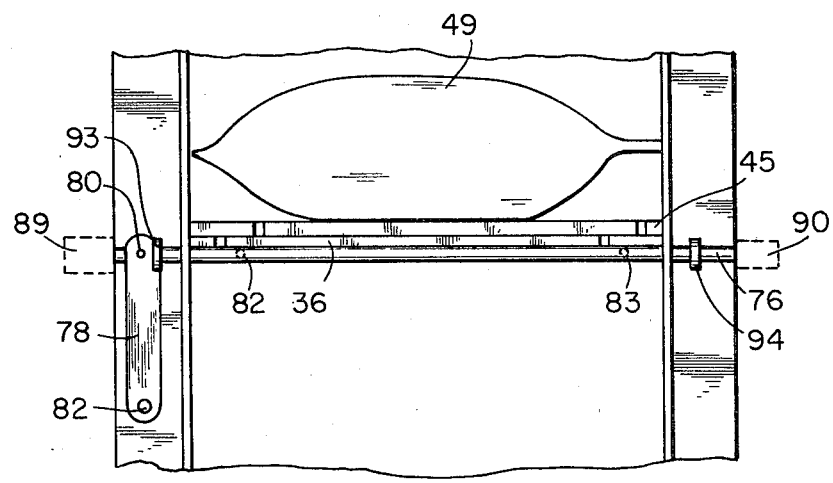
FIG. 5 is a fragmentary side view taken along the lines 5—5 of FIG. 1 and viewed in the direction of the arrows.

The downward movement of shelves 36 through 39 and trays 45 through 48 is controlled by a plurality of fingers or pins alignable with slots provided in the shelves and trays. Top shelf 40 is not provided with slots but will compress bag 52 in a manner similar to the compression of bags 49–51 by shelves 37–39. Fingers 82 and 83 (FIG. 3) are fixedly mounted to bar 76 slidably mounted to beams 23 and 24. Likewise, a pair of fingers 91 and 92 are fixedly mounted to bar 77 in turn slidably mounted to beams 22 and 25. Bars 76 and 77 are interconnected to operate as a unit by means of axle 82 rotatably mounted to beams 24 and 25 and connected to the bars by means of links 78 and 79 in turn connected by pins 80 and 81 to bars 76 and 77. Shown in FIG. 5, bar 76 is connected by pin 80 to the top end of link 78 in turn having a bottom end connected to axle 82. A conventional solenoid 89 may be mounted to one end of axle 76 to control movement of the two bars. Likewise, a handle 90 may be attached to the opposite end of the bar to allow manual movement of both bars 76 and 77. Movement of bar 76 results in the same movement of bar 77 due to the axle link connection. A pair of stops 93 and 94 are fixedly mounted to bar 76 near beams 24 and 23 to limit the amount of movement of the bar relative to the vertical beams. Thus, the bars are not accidentally unmounted from the vertical beams. Stops 93 and 94 are located sufficiently apart from beams 24 and 23 to allow the pins 82 and 83 to move and become aligned with the slots provided in the shelves and trays.

Each shelf 36 through 39 includes four slots. For example, shelf 36 (FIG. 3) includes a pair of aligned slots 84 and 96 and a second pair of aligned slots 85 and 97. Normally, pins 82, 83, 91 and 92 are positioned beneath and adjacent shelf 36 to support the entire secondary frame 35 along with the trays and bags positioned thereatop. By movement of bars 76 and 77 rearwardly, pins 82, 83, 91 and 92 will become aligned with slots 84, 85, 97 and 96 allowing the secondary frame to drop downwardly while the pins immediately contact and support tray 54 normally resting atop shelf 36. Shelf 36 is shown fragmented at location 86 (FIG. 3) to illustrate the slots provided in tray 45. Four slots 87, 88, 99 and 100 are provided in tray 45 being offset from the slots of shelf 36 and being aligned to allow pins 82, 83, 91 and 92 to pass there through when bars 76 and 77 are moved forwardly.

Figure 4:
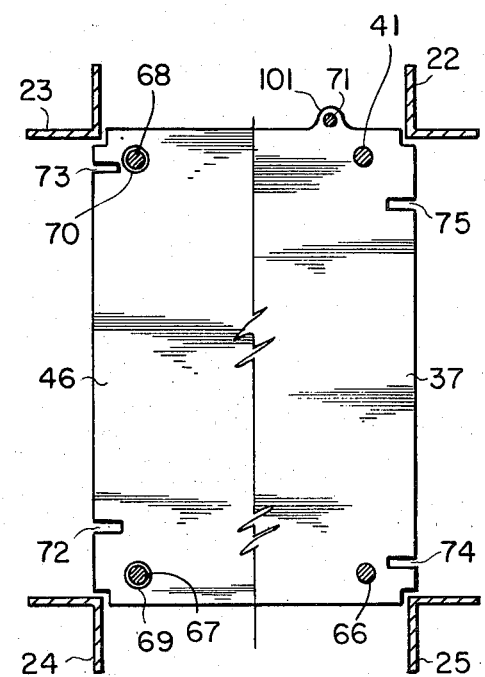
FIG. 4 is an enlarged cross-sectional view taken along the lines 4—4 of FIG. 1 and viewed in the direction of the arrows.

FIG. 4 is a cross-sectional view showing one-half of shelf 37 having slots 74 and 75 provided in the right hand edge portion and with rods 41 and 66 fixedly attached to shelf 37 and extending downwardly being attached to shelf 36 and extending freely through tray 45. Each tray includes rod apertures to allow the rods to extend freely therethrough ensuring that the trays fall or move independently of secondary frame 35. For example, the left hand portion of tray 46 is depicted in FIG. 4 as having a pair of apertures 69 and 70 through which rods 67 and 68 extend freely being fixedly attached to shelves 37 and 38. Slots 72 and 73 are also shown in the left hand edge portion of tray 46. Actuator 71 is fixedly mounted to shelf 37 and positioned outwardly of the tray to not interfere with movement of the tray. An ear 101 may be provided on each shelf for the mounting of actuator 71 to ensure a noninterference between the actuator and adjacent tray. It should be further noted that a right angle recess is provided at the four corners of the shelves and trays to complementary receive the right angle corner of each vertical beam 22 through 25 to guide the secondary frame and trays during vertical movement of the frame and trays relative to the beams.

Below each bag and above the shelves are movable plates or trays whose function is to intermittently support each bag while the framework and all supported bags fall. Compression of each bag between the tray and framework shelf results in the infusion of the fluid from the bag into the abdomen. Likewise, release of the emptied tray and support of the secondary frame accomplished by the support bar pins moving through the slots, allows drainage of individual bags from the patient. Prevention of outflow from each bag is performed by the clamps engaging the nipples or tubular ports of each bag. The clamps are normally held in a closed position by the weight of each bag. Removal of the weight on such clamps by separation of the appropriate tray and supporting shelf allows selective opening of the bag to be infused. The clamps also function to ensure that a bag is closed after drainage only when it has reached a certain minimum weight such as 80% of its original weight. Thus, a safety mechanism is provided for preventing over infusion of the abdomen since fluid infused towards the abdomen is directed towards the bag which does not receive a proper weight of fluid.

Figure 7:
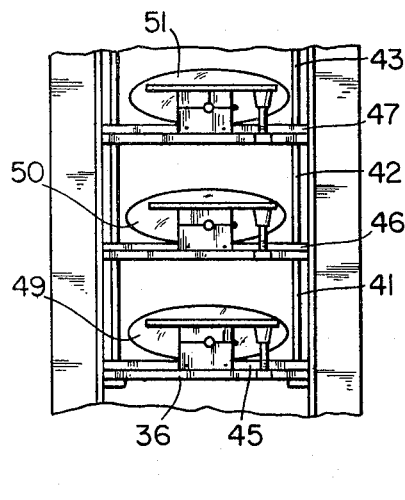
FIG. 7 is a fragmentary diagram depicting the initial setting of the cycler of FIG. 1.
Figure 8:
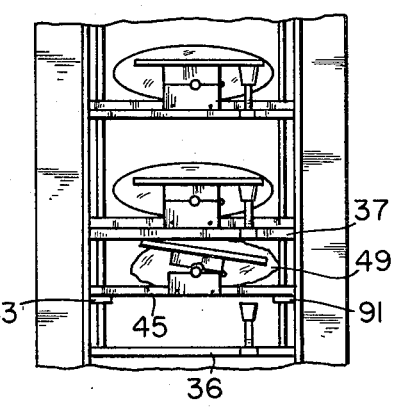
FIG. 8 is the same view as FIG. 7 only showing the first bag being compressed forcing fluid towards the patient.
Figure 9:
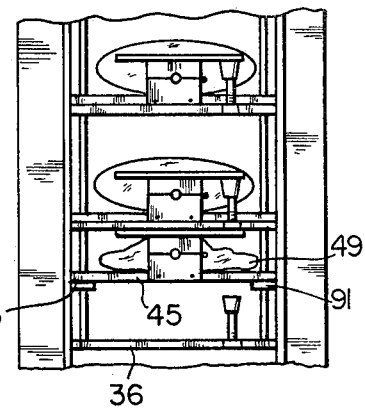
FIG. 9 is the view as FIG. 8 only showing the first bag of fluid in the completely compressed state.
Figure 10:
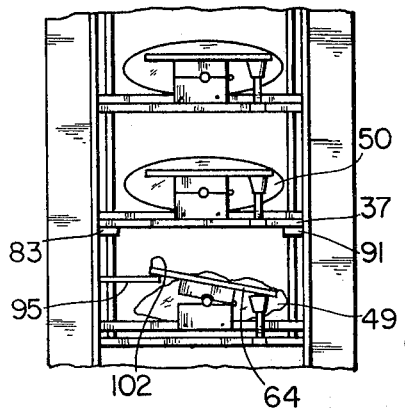
FIG. 10 is the same view as FIG. 9 only showing the first tray and bag in the dropped position receiving fluid back from the patient.

To utilize the STS-GPC, the patient removes four to six, two-liter bags of dialysate from the shipping container. Each bag is then placed above trays 45 through 48 and the nipple or outlet portions of each bag is clamped by clamps 55 through 58. The clamps are opened by lifting the bar mounted to the top half portion of each clamp. Releasing the bar allows the weight of the bag pushing downwardly on the tray and thus shelf to close the clamp by lever action with the actuators contacting the bar. For example, positioning of bag 49 upon tray 45 results in downward pressure applied to shelf 36 in turn contacting actuator 65 with end 98 of bar 64 closing clamp 55. Thus, at this point each bag will remain closed with the framework and bags being supported. A spike is then inserted into each bag from the tubing set which connects all bags together. In the example shown, four bags are interconnected; however, it is to be understood that less than four or more than four bags may be interconnected depending upon the number of shelves and trays provided in the device. The overall size of the tubing set is approximately 25 inches by 8 inches in the extended position. The insertion of the spike is made easy by the immobilization of the tubular port and each bag clamp. The common end of the tubing set is then attached to the patient line leading to the patient with sterile precautions. Control rods 76 and 77 are then actuated by moving them rearwardly approximately ½ inch. The movement may be accomplished either manually or by electronic solenoid. Movement of the bars or control rods allows shelf 36 and the secondary frame 35 to fall from the position depicted in FIG. 7 to the position depicted in FIG. 8. Bag 49 is then compressed between shelf 37 and tray 45 with the entire weight of secondary frame 35 and the bags supported thereon being forced downwardly against bag 49. Bag clamp 55 is opened by the separation of actuator 65 from end 98 of bar 64. Infusion of bag 49 is accomplished in approximately five to ten minutes. After a predetermined time or dwell of the fluid in the abdomen, the position control bar 76 and 77 are then moved forwardly approximately ½ inch and tray 45 is allowed to fall from the compressed position in FIG. 9 to the downward position shown in FIG. 10. Shelf 37 of secondary frame 35 contacts bar 64 closing clamp 55 in FIG. 9 and stopping fluid flow from bag 49.

Pins 83 and 91 contact the second shelf 37 again supporting secondary frame 35 along with the trays and bags positioned thereon. By again holding secondary frame 35, the compression force is removed from bag 49. A cantileveredly mounted pin 95 secured to the main frame (FIG. 1) contacts end 102 (FIG. 10) of bar 64 holding the clamp in the upward position. Pin 95 prevents the first bag clamp from closing in spite of the increasing weight of the bag as the fluid from the patient drains by force of gravity back into bag 49. Pin 95 is thus an actuator on the main frame which is operable to hold clamp 55 once tray 45 is beneath pins 83 and 91 in an open position allowing fluid flow into bag 49. Eventually tray 45 will contact shelf 36 with bar 64 moving past pin 95 contacting actuator 65. Actuator 65 is therefore operable to contact and close clamp 55 when beneath pins 83 and 91 stopping fluid flow into bag 49.

Figure 11:
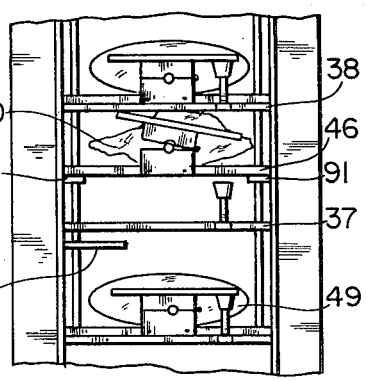
FIG. 11 is the same view as FIG. 10 only showing the second bag of fluid being compressed for outward flow.
Figure 12:
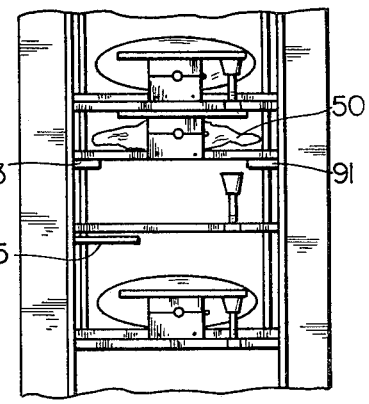
FIG. 12 is the same view as FIG. 11 only showing the second bag in the completely compressed state.

After a preset length of flow from the patient to bag 49, such as 15 minutes, the control bars 76 and 77 are moved to allow shelf 37 and the attached secondary frame 35 to fall downwardly while control pins engage and support the second tray 46 (FIG. 11). The entire weight of the secondary frame 35 along with the bags and trays supported thereon is then applied via shelf 38 to bag 50 with the bag being compressed forcing the fluid outwardly through the tubular port with clamp 56 pivoted to the open position. Again, bag 50 is completely compressed as shown in FIG. 12 and the process is repeated allowing tray 46 to fall downwardly thereby refilling the second bag 50 and subsequently compressing and refilling the remaining bags until the process is completed.

Timing of inflow, dwell and outflow may be variably adjusted. A safety mechanism for overinfusion exists, because, if for example, the first bag does not fill with an appreciable amount of fluid then its clamp would not close and the inflow fluid from the second bag would be diverted in part to the first bag. The device progressively progresses and drains each layer with minimal external energy being required for each infusion and drainage. A further modification of the device is that a small heating lamp is placed at the position just above the position control bars where each bag rests prior to infusion.

The cycler machine disclosed herein has been developed for infusion and withdrawal of fluid from the peritoneal cavity of patients; however, it is to be understood that the device may be used for infusion and withdrawal of other fluids for a variety of medical reasons. The machine is particularly advantageous to perform continuous cyclic peritoneal dialysis during which 8 to 12 liters of fluid is moved through the patients abdominal cavity during sleeping hours with a residual 2 liters left in the peritoneal cavity during daytime. The machine may also be used for continuous equilibrium peritoneal dialysis in which fluid is cycled into and out of the abdomen in 2 liter volumes during a 24 hour period. A dwell time of 4 hours for each exchange in the abdominal cavity may be scheduled.

Many advantages of the subject invention will apparent from the above description. In particular, a short tubing set may be used for connection of the 4 to 6 bags with a maximum tubing dimension of 25 inches by 8 inches. Further, the two liter volumes of fluid are removed from and returned to the same two liter bags thus obviating need for a large 8 to 12 liter drainage bag located near the floor. The bag clamping mechanism works by gravity weight of each bag rather than by electronics thus simplifying operations. In addition power for the machine is generated strictly by gravity thus minimizing the power requirements. The machine is considerably more compact and easy to assemble as compared to prior devices. In addition, the bags of peritoneal fluid are firmly affixed into the machine at hand and waist level thus simplifying insertion of tubing spikes into the bags. As mentioned, the machine disclosed herein does not require fluid collection bags nor fluid warming bags. A simpler set up is accomplished without handling of tubing and bags. Further, more immobility of the bag nipples or tubular ports is provided assisting in spike insertion into the bags. In view of the short tubing set, the possibility exists of providing preconnecting tubing from the factory in the same shipping container for six fluid bags thus allowing nighttime cycling of pertonial dialysis with only one spike connection tubing set. As previously mentioned, automatic protection from abdomen overfill by a simple mechanical mechanism is accomplished. When compared to the reverse osmossis proportioning peritoneal machine, the system offers considerably reduce set-up time, much less complexity and lower machine costs.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A cycling machine for infusion and withdrawal of fluid from a person comprising:
   main frame means;
   secondary frame means slidably mounted on said main frame means and including a plurality of shelves, a vertical stack of trays each resting atop an associated shelf of said plurality of shelves with said trays being spaced apart, a bag of fluid on each of said trays;
   stop means movably mounted on said main frame means initially positioned beneath said stack and releasably engageable with said secondary frame means and also releaseably engageable with the most adjacent tray of said stack to hold said adjacent tray as said secondary frame means and supported trays and bags fall downwardly pressing said associated bag against said adjacent tray squeezing fluid therefrom;
   operator means engaged with said stop means and cyclically operable until all of said bags are drained and refilled to first release said stop means from said secondary frame means which falls while said stop means holds said adjacent tray and to next move said stop means apart from said adjacent tray to catch and hold said secondary frame means allowing said adjacent tray to fall back atop said associated shelf decompressing said associated bag to receive gravity inflow of fluid.

2. The machine of claim 1 and further comprising clamping means engageable with each bag and operable to allow fluid flow from a bag on said adjacent tray only when said adjacent tray is held by said stop means.

3. The machine of claim 2 and further comprising additional means engageable with said clamping means to allow fluid flow into said bag on said adjacent tray when said adjacent tray falls from said stop means.

4. The machine of claim 1 wherein:
   said secondary frame means includes means fixedly connecting said shelves together, and said main frame means and said secondary frame means include cooperating guide means operable to vertically guide said secondary frame means.

5. The machine of claim 4 wherein:
   each shelf and each tray includes pin passages with said passages on each tray non-aligned with said passages on an adjacent shelf;
   said stop means includes pins positionable beneath and against each shelf and each tray and alignable by said operator means with said pin passages to allow each shelf and each tray to fall past said pins.

6. The machine of claim 5 wherein:
   said operator means includes a pair of control rods slidably mounted on said main frame means and having said pins mounted thereon projecting inwardly beneath said shelves and trays, said control rods are interconnected to slide horizontally in unison.

7. The machine of claim 6 and further comprising:
   clamp means including a clamp associated with each tray and engageable with a bag on each tray to control fluid flow therefrom and thereto.

8. The machine of claim 7 wherein:
   said clamp means includes first actuator means on said secondary frame means operable to move each clamp to a closed position stopping fluid flow from a bag on each shelf, said clamp means further includes a second actuator on said main frame means operable to hold said clamp on said adjacent tray once beneath said pins in an open position allowing fluid flow into a bag.

9. A short tube set gravity powered peritoneal cycler comprising:
   main frame means;
   a plurality of bags of fresh fluid;
   a plurality of trays each sized to support one of said bags;
   vertical frame means slidably mounted in said main frame means and having mounting planes each receiving one of said trays;
   a movable holder on said main frame means to alternately hold a particular tray with bag as said vertical frame means weighs downwardly thereon squeezing fresh fluid therefrom and then holding said vertical frame means as said particular tray falls away from said vertical frame means decompressing said bag on said particular tray which receives back waste fluid.

10. The cycler of claim 9 and further comprising clamping means engageable with each bag and operable to control fluid flow therefrom and thereto.

11. The cycler of claim 10 wherein said mounting planes are fixedly connected together supporting said trays.

12. The cycler of claim 10 wherein said holder includes fingers movably mounted to said main frame means releasably engageable alternately with said trays and planes.

13. A short tube set gravity powered peritoneal cycler for operation with full bags of fluid comprising:
   main frame means;
   a plurality of trays each sized to support a full bag of fluid;
   vertical frame means slidably mounted in said main frame means and having mounting planes each receiving one of said trays and spacing said trays apart a distance at least equal to a full bag thickness;
   a movable holder on said main frame means to alternately hold a particular tray as said vertical frame means moves downwardly decreasing said distance between said particular tray and the tray thereabove and then holding said vertical frame means as said particular tray falls away from said vertical frame means until said distance is once again attained.

14. The cycler of claim 13 wherein said mounting planes are fixedly connected together supporting said trays.

15. The cycler of claim 13 wherein said holder includes fingers movably mounted to said main frame means releasably engageable alternately with said trays and planes.

16. A cycling machine for controlling flow of fluid between a person and bags of fluid comprising:
   main frame means;
   secondary frame means slidably mounted to said main frame means;
   a plurality of trays mounted on said secondary frame means and each spaced apart at least a distance equal to the thickness of a bag of fluid;
   a stop means movably mounted relative to said main frame means and said secondary frame means and initially positioned beneath said trays and releasably enagageable with said secondary frame means and the most adjacent of said trays to hold said adjacent tray as said secondary frame and supported trays fall downwardly depressing any bag on said adjacent tray; and,
   operator means engaged with said stop means and cyclically operable to first release said stop means from said secondary frame means which falls while said stop means holds said adjacent tray and to next move said stop means apart from said adjacent tray allowing said adjacent tray to fall back atop said secondary frame means.

* * * * *